(12) United States Patent
Canter (10) Patent No.: US 7,845,945 B2
(45) Date of Patent: *Dec. 7, 2010

(54) ANCHORING ELEMENT FOR USE IN BONE (75) Inventor: Stanton R. Canter, 19274 Berclair La., Tarzana, CA (US) 91356

(73) Assignee: Stanton R. Canter, Woodland Hills, CA (US)

( * ) Notice: Subject to any disclaimer, the term of this patent is extended or adjusted under 35 U.S.C. 154(b) by 50 days.

This patent is subject to a terminal disclaimer.

(21) Appl. No.: 11/035,266

(22) Filed: Jan. 12, 2005

(65) Prior Publication Data

US 2005/0164146 A1 Jul. 28, 2005

Related U.S. Application Data

(60) Provisional application No. 60/539,633, filed on Jan. 28, 2004.

(51) Int. Cl.
*A61C 8/00* (2006.01)

(52) U.S. Cl. ...................................... 433/173

(58) Field of Classification Search ............. 411/411, 411/414, 418, 424, 426; 606/72, 73; 433/172–174, 433/180, 175, 176

See application file for complete search history.

(56) References Cited

U.S. PATENT DOCUMENTS

| 3,499,222 | A |   | 3/1970 | Edelman et al. |
|---|---|---|---|---|
| 3,732,621 | A |   | 5/1973 | Bostrom |
| 3,866,510 | A | * | 2/1975 | Eibes et al. ............ 411/418 |
| 4,180,910 | A |   | 1/1980 | Straumann et al. |
| 4,359,318 | A |   | 11/1982 | Gittleman |
| 4,447,209 | A |   | 5/1984 | Sutter |
| 4,531,916 | A |   | 7/1985 | Scantlebury et al. |

(Continued)

FOREIGN PATENT DOCUMENTS

EP 1 145 691 A 4/2000

(Continued)

OTHER PUBLICATIONS

International Search Report for PCT Application No. PCT/US2005/002717 filed Jan. 28, 2005.

(Continued)

*Primary Examiner*—Cris L Rodriguez
*Assistant Examiner*—Sunil K Singh
(74) *Attorney, Agent, or Firm*—Blakely Sokoloff Taylor & Zafman, LLP (57) ABSTRACT

An anchoring element for use in bone has a proximal end and a distal end. The distal end may be embedded in bone with the proximal end exposed. An abutment surface is disposed toward the proximal end. The anchoring element includes four surfaces that define the distal end. A generally cylindrical first surface defines an exterior of the anchoring element and includes a first external thread having a pitch. An annular second surface is disposed toward the distal end and joined to the first surface along an outer circumference of the second surface. A third surface concentric with the first surface is joined to the second surface along an inner circumference of the second surface. A fourth surface disposed between the distal end and the proximal end of the first surface is joined to the third surface along an outer circumference of the fourth surface.

16 Claims, 6 Drawing Sheets

U.S. PATENT DOCUMENTS

| | | | |
|---|---|---|---|
| 4,657,510 A | 4/1987 | Gittleman | |
| 4,790,753 A * | 12/1988 | Fradera | 433/174 |
| 4,960,381 A | 10/1990 | Niznick | |
| 4,960,391 A | 10/1990 | Beinhaur | |
| 5,061,181 A | 10/1991 | Niznick | |
| 5,071,351 A | 12/1991 | Green | |
| 5,076,788 A | 12/1991 | Niznick | |
| 5,259,398 A | 11/1993 | Vrespa | |
| 5,312,256 A | 5/1994 | Scortecci | |
| 5,366,374 A | 11/1994 | Vlassis | |
| 5,433,607 A | 7/1995 | Schmid et al. | |
| 5,470,230 A * | 11/1995 | Daftary et al. | 433/174 |
| 5,503,187 A | 4/1996 | Simmons et al. | |
| 5,571,017 A | 11/1996 | Niznick | |
| 5,591,029 A | 1/1997 | Zuest | |
| 5,622,500 A * | 4/1997 | Niznick | 433/173 |
| 5,667,384 A | 9/1997 | Sutter | |
| 5,702,346 A | 12/1997 | Lazzara et al. | |
| 5,762,500 A | 6/1998 | Lazarof | |
| 5,816,813 A | 10/1998 | Hansson et al. | |
| 5,871,356 A | 2/1999 | Guedj | |
| 5,989,028 A | 11/1999 | Niznick | |
| 6,213,775 B1 * | 4/2001 | Reipur | 433/173 |
| 6,287,117 B1 | 9/2001 | Niznick | |
| 6,394,809 B2 * | 5/2002 | Rogers et al. | 433/174 |
| 6,953,426 B2 * | 10/2005 | Barber et al. | 600/7 |
| 2001/0004711 A1 | 6/2001 | Lazzara et al. | |
| 2002/0160335 A1 | 10/2002 | Ashman et al. | |
| 2005/0042574 A1 * | 2/2005 | Lazarof | 433/174 |
| 2005/0164146 A1 | 7/2005 | Cantor | |
| 2006/0115791 A1 | 6/2006 | Carvalho | |
| 2007/0292820 A1 | 12/2007 | Canter | |
| 2008/0003539 A1 | 1/2008 | Lundgren | |
| 2008/0044794 A1 | 2/2008 | Brajnovic | |
| 2009/0081612 A1 * | 3/2009 | Jorneus et al. | 433/173 |

FOREIGN PATENT DOCUMENTS

| | | |
|---|---|---|
| EP | 1952781 A3 | 9/2008 |
| FR | 2 737 847 A | 2/1997 |
| FR | 2783700 | 3/2000 |
| GB | 1 203 093 | 8/1970 |
| WO | WO 91/14404 | 10/1991 |
| WO | WO 01/26579 | 4/2001 |
| WO | WO 2005/072640 A1 | 8/2005 |
| WO | WO 2005/084578 A1 | 9/2005 |

OTHER PUBLICATIONS

International Preliminary Report on Patentability for Application No. PCT/US2005/002717 filed Jan. 28, 2005.

European Examination Report dated Dec. 8, 2006 for Application No. EP05706134 filed Jan. 28, 2005.

International Search Report for PCT Application No. PCT/SE2005/000308 filed Mar. 3, 2005.

International Preliminary Report on Patentability for PCT Application No. PCT/SE2005/000308 filed Mar. 3, 2005.

European Examination Report dated Sep. 3, 2007 for Application No. EP05722178 filed Mar. 3, 2005.

European Search Report for European Application No. EP08005017 filed Jan. 28, 2005.

European Search Opinion for European Application No. EP08005017 filed Jan. 28, 2005.

United States Office Action dated Jul. 26, 2010 for co-pending U.S. Appl. No. 10/587,497, filed on Jul. 20, 2007 entitled Anchoring Element for Use In Bone.

* cited by examiner

ANCHORING ELEMENT FOR USE IN BONE

CROSS-REFERENCE TO RELATED APPLICATION

This application claims the benefit of U.S. Provisional Patent Application No. 60/539,633 filed on Jan. 28, 2004.

BACKGROUND OF THE INVENTION

Anchoring elements are used in a variety of dental, medical, and surgical procedures where it is desired to embed a mechanical attachment into living bone. One example of a procedure that uses anchoring elements is dental prosthesis using embedded implants.

Dental implants provide a desirable prosthesis for patients who are missing one or more natural teeth. A dental implant includes an anchoring element that is embedded into the jawbone and a prosthetic tooth that is attached to and supported by the anchoring element. The prosthetic tooth may be attached directly to the anchoring element or an abutment fixture may be attached to the anchoring element and support the prosthetic tooth in turn. An appropriate anchoring element will support bone growth that invades the anchoring element such that the anchoring element becomes integrated with the surrounding bone in a process termed osseointegration.

An anchoring element to support a prosthetic tooth may be embedded in what is termed a two-stage procedure. In the first stage, the anchoring element is embedded into the jawbone and the surgical site is then closed. After a period of months the anchoring element will achieve osseointegration. The site of the anchoring element is then re-opened surgically to allow the attachment of a prosthetic tooth.

More recently techniques have been developed that permit a dental implant to be embedded in a one-stage procedure. In a one-stage procedure, the anchoring element is embedded and a prosthetic tooth is immediately fitted. The immediately fitted prosthetic tooth may be an interim prosthesis that allows the soft tissue to properly heal and maintains the spacing and alignment of adjacent teeth during the period of osseointegration. A permanent prosthetic tooth may be fitted at a later date after at least some osseointegration has occurred without requiring an additional surgical procedure.

To achieve successful osseointegration it is necessary that the anchoring element fit closely into the surrounding bone, generally having a gap of no more than 1.5 millimeters. It is also important that the anchoring element not move relative to the surrounding bone during the period of osseointegration. Where the anchoring element cannot be closely fitted to the surrounding bone, it may be necessary to use bone-grafting materials to fill the space between the anchoring element and the surrounding bone.

Molars are commonly missing teeth. The use of an implant to replace a molar presents some special difficulties. Molars generally have multiple roots. The mandibular molars of the lower jaw generally have two roots. The maxillary molars of the upper jaw generally have three roots. In a fresh extraction site the void left by the molar roots presents a site that can be difficult to fit with an anchoring element. In addition, the bone in the molar region of the jaw generally consists of a thin hard layer of cortical bone surrounding a core of softer spongy cancellous bone. The cancellous bone may provide poor support for the anchoring element prior to osseointegration.

A molar is a relatively large tooth and it is desirable to use an anchoring element having a relatively large diameter to fill the void following an extraction. However, the use of a wide anchoring element may require that a significant amount of bone be removed from the extraction site to accommodate the anchoring element. This may leave only a small amount of cortical bone available to support the anchoring element which may be embedded in predominantly cancellous bone. In particular, the use of a wide anchoring element may require removal of the triangular mound-shaped mass of bone that is found between the roots known as the interradicular bone. Thus, it is difficult to place an anchoring element in a fresh molar extraction site with sufficient stability to allow embedding of a dental implant with a one-stage procedure.

Another circumstance that can present difficulties in placing an anchoring element for a dental implant occurs in cases where it is desired to place a dental prosthesis in a healed extraction site. When a molar is lost, the alveolar ridge that supports the teeth is fairly rapidly resorbed. This causes a loss of height of the jawbone in the area of tooth loss. When an anchoring element is to be embedded in a healed extraction site, it may not be possible to place an anchoring element to a very great depth.

In the lower jaw, the presence of the mandibular alveolar nerve in the lower jaw limits the depth of the anchoring element. In the upper jaw the maxillary sinus limits the depth. These limiting anatomical features may require the use of a short anchoring element, perhaps 5 to 8 millimeters in length. The use of short anchoring elements for such cases has a lower rate of long-term success because of the reduced surface area available for osseointegration.

It would be desirable to have an anchoring element that can be used to place a dental implant in the molar area both for fresh extraction sites and for healed sites.

SUMMARY OF THE INVENTION

An anchoring element for use in bone has a proximal end and a distal end. The distal end may be embedded in bone with the proximal end exposed. An abutment surface is disposed toward the proximal end. The anchoring element includes four surfaces that define the distal end. A generally cylindrical first surface defines an exterior of the anchoring element. At least a portion of the first surface includes a first external thread having a pitch. An annular second surface is disposed toward the distal end and the first surface is joined to the second surface along an outer circumference of the second surface. A third surface concentric with the first surface is joined to the second surface along an inner circumference of the second surface. At least a portion of the third surface may include an internal thread having the pitch of the first external thread. A fourth surface disposed between the distal end and the proximal end of the first surface is joined to the third surface along an outer circumference of the fourth surface.

In another embodiment, an anchoring element includes six surfaces that define the distal end. At least a portion of a first surface includes a first external thread. An annular second surface is disposed toward the distal end and joined to the first surface along an outer circumference of the second surface. A third surface concentric with the first surface is joined to the second surface along an inner circumference of the second surface. An annular fourth surface is disposed between the distal end and the proximal end and joined to the third surface along an outer circumference of the fourth surface. A fifth surface concentric with the first surface is joined to the fourth surface along an inner circumference of the fourth surface. A sixth surface is disposed toward the distal end and joined to the fifth surface along an outer circumference of the sixth surface.

In another embodiment, an anchoring element for use in bone has a proximal end and a distal end. The distal end may be embedded in bone with the proximal end exposed. The anchoring element includes a generally cylindrical first surface, at least a portion of the first surface including an external thread. An abutment surface is disposed at the proximal end of the anchoring element. The abutment surface is at an angle to an axis from the proximal end to the distal end of the anchoring element.

DETAILED DESCRIPTION OF THE INVENTION

Figures 1, 2, 3, 4, 5, 6, 7, 8:
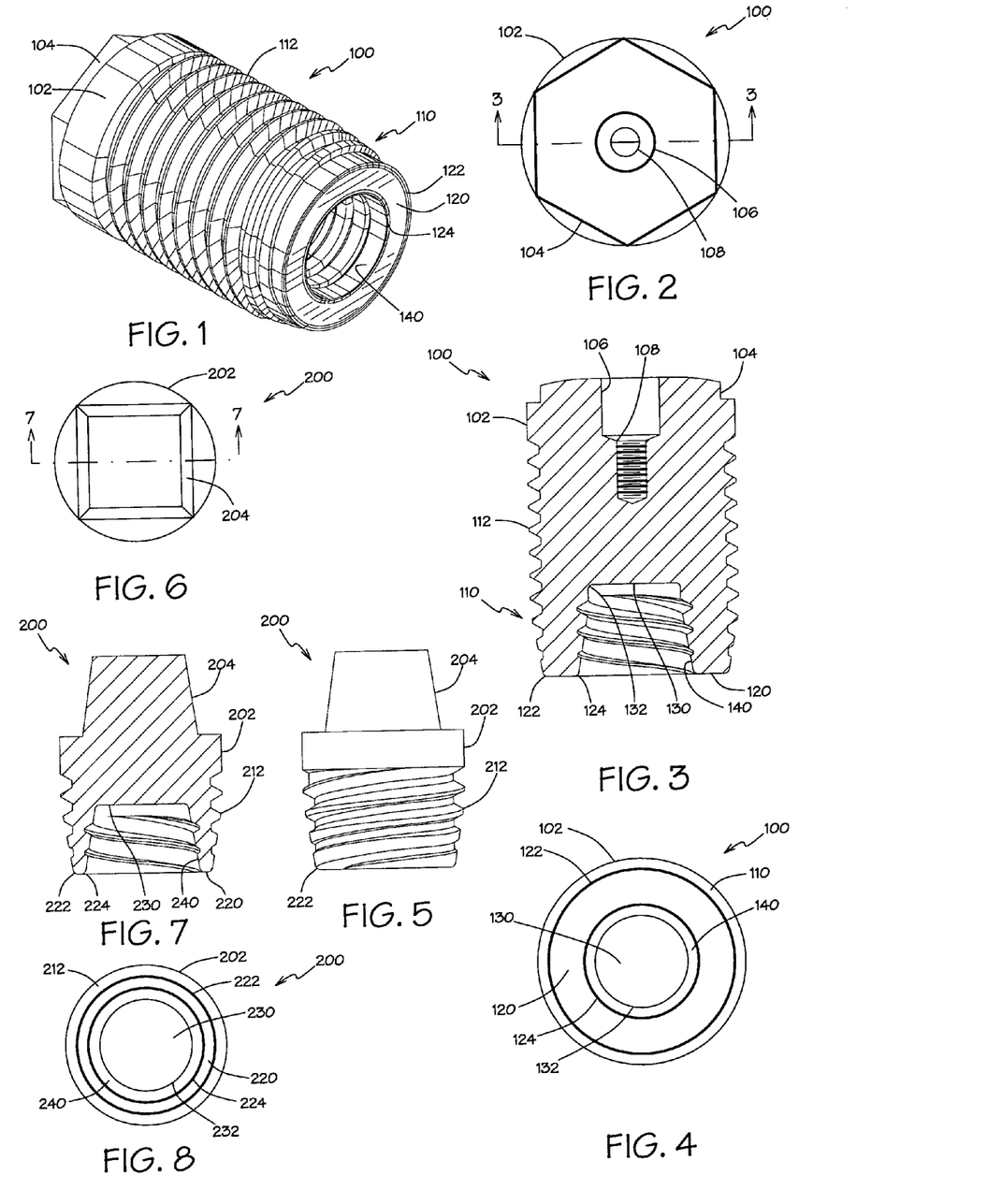
FIG. 1 is a pictorial view of an anchoring element for use in bone that embodies the invention.
FIG. 2 is a plan view of the distal end of the anchoring element shown in FIG. 1.
FIG. 3 is a cross section of the anchoring element taken along the line 3-3 shown in FIG. 2.
FIG. 4 is a plan view of the distal end of the anchoring element of FIGS. 1 through 3.
FIG. 5 is a side elevation of another anchoring element that embodies the invention.
FIG. 6 is a plan view of the proximal end of the anchoring element of FIG. 5.
FIG. 7 is a cross section taken along section line 7-7 shown in FIG. 6.
FIG. 8 is a plan view of the proximal end of the anchoring element of FIGS. 5 through 7.
Figure 9:
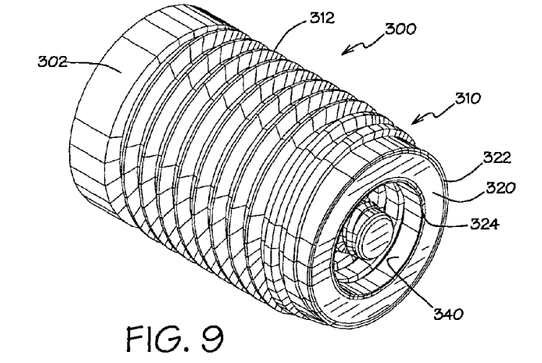
FIG. 9 is a pictorial view of another anchoring element that embodies the invention.

FIG. 1 shows an anchoring element 100 for use in bone that embodies the invention. The anchoring element may be fabricated of any biocompatible material known or discovered to promote osseointegration such as titanium or a titanium alloy. The portions of that are to be in intimate contact with bone can display various surface characteristics. These portions can be titanium plasma sprayed, coated with hydroxy-apatite (HA coated), surface machined, sand blasted, or acid etched to promote osseointegration.

For convenience in description, the anchoring element 100 will be described with reference to a distal end and a proximal end. The distal end is shown in FIG. 1 as the end to the lower right and is the end that is embedded to the greatest depth in bone. The proximal end is the end to the upper left and is the end that may be exposed when the anchoring element 100 is embedded in bone.

The anchoring element 100 includes a first surface that is a generally cylindrical exterior surface of the anchoring element. The term "generally cylindrical" is used to describe a surface that is substantially rotationally symmetric about an axis that extends from the distal end to the proximal end. The first surface may include a screw thread 112. It will be appreciated that a screw thread is not rotationally symmetric in the strictest sense. A screw thread or similar feature is intended to be included by the term "substantially rotationally symmetric." The exterior surface of the anchoring element 100 may include features such as the aforementioned screw thread and other features such as shoulders 102, tapered portions 110, and the like, all of which are intended to be included by the term "generally cylindrical."

At least a portion of the first surface of the anchoring element 100 may include a first external thread 112 having a pitch. The thread 112 may be of any of a variety of forms known or discovered to be effective for embedding the anchoring element in bone. The thread 112 may include self-threading (thread cutting) features or other features that aid in embedding the anchoring element into bone or that promote osseointegration.

The first surface may include a frustrated first conical portion 110 adjacent the distal end of the anchoring element 100 such that a smaller circumference of the first conical portion is adjacent the distal end. The first conical portion 110 may facilitate placing the anchoring element 100 into a hole that is prepared in the bone to receive the anchoring element. The first conical portion 110 may provide a somewhat smaller leading distal end that allows the anchoring element 100 to initially engage the bone with minimal force and align the anchoring element to the hole that has been prepared in the bone.

The first conical portion 110 may be unthreaded or may partially or fully intersect the first external thread 112. In one embodiment the first conical portion 110 may have a smallest diameter at the distal end of the anchoring element 100 that is approximately a root diameter of the first external thread. The first conical portion 110 may gradually increase in diameter toward the proximal end thereby providing a gradually increasing thread depth.

The anchoring element 100 may include an abutment surface disposed toward the proximal end of the first surface. The abutment surface may be of any of a variety of known or discovered forms that permit attachment to the anchoring element.

FIGS. 1 through 3 illustrate an abutment surface that may be provided to receive a dental prosthesis. The illustrated abutment surface includes an external hex surface 104 that may provide a wrenching surface for embedding the anchoring element 100. The illustrated abutment surface further includes a locating recess 106 and an internal anchoring thread 108 to receive a devices that is coupled to the anchoring element by a screw.

The anchoring element 100 includes an annular second surface 120 disposed toward the distal end of the first surface and joined to the first surface along an outer circumference 122 of the second surface. The second surface 120 may engage the bottom of the hole that has been prepared in the bone and thereby contribute significantly to the stability of the embedded anchoring element 100. The second surface 120 may be substantially flat or may have a rounded or other shape chosen to effectively cooperate with the bottom of the hole that has been prepared in the bone to provide initial stability.

As may be seen in the plan view of the distal end, the anchoring element 100 includes a third surface 140 concentric with the first surface and joined to the second surface 120 along an inner circumference 124 of the second surface. At least a portion of the third surface 140 may include an internal thread having the pitch of the first external thread such that both threads will advance the anchoring element 100 at the same rate as it is rotated to embed the anchoring element into bone. The internal thread may be of any of a variety of forms known or discovered to be effective for embedding the anchoring element in bone. The internal thread may include self-threading (thread cutting) features or other features that aid in embedding the anchoring element into bone or that promote osseointegration. It is contemplated that the hole in the bone that is prepared to receive the anchoring element 100 may leave residual bone in place such that the third surface 140 will at least partially engage the bone to provide additional initial stability and an additional surface for osseointegration.

The third surface 140 may include a frustrated second conical portion adjacent the distal end such that a larger circumference of the second conical portion is adjacent the distal end. The second conical portion may facilitate placing the anchoring element 100 into the portion of hole that includes residual bone. The second conical portion may compress the residual bone as the anchoring element 100 is embedded to further increase initial stability.

The second conical portion may be unthreaded or may partially or fully intersect the first internal thread. In one embodiment the second conical portion may have a largest diameter at the distal end of the anchoring element 100 that is approximately a root diameter of the first internal thread. The second conical portion may gradually increase in diameter toward the proximal end thereby providing a gradually increasing thread depth.

The anchoring element 100 includes a fourth surface 130 disposed between the distal end and the proximal end and joined to the third surface 140 along an outer circumference of the fourth surface 132. It is contemplated that the hole in the bone that is prepared to receive the anchoring element 100 may leave an upper surface on the residual bone such that the fourth surface 130 will engage the upper surface to provide additional initial stability and an additional surface for osseointegration.

FIG. 3 is a cross-section of the anchoring element 100 taken along a diameter as shown by the section line 3-3 in FIG. 2. FIG. 3 may aid in visualizing the relationships between the various surfaces of the anchoring element 100. FIG. 3 may also aid in visualizing a possible interaction of the conical sections with the threads at the distal end.

FIGS. 5 through 8 illustrate another anchoring element 200 that embodies the invention. This embodiment includes many features that are similar to the anchoring element 100 illustrated by FIGS. 1 through 4. Similar features for anchoring element 200 have been given reference numerals that are the reference numerals used for anchoring element 100 increased by 100.

In this embodiment the anchoring element 200 includes an abutment surface 204 in the form of a frustrated square pyramid. The abutment surface 204 may provide a wrenching surface. If the anchoring element is used to support a dental prosthesis, a prosthetic tooth may be directly coupled to the abutment surface 204 such as by cement.

FIG. 7 shows a cross section of the anchoring element 200 taken along the section line 7-7 as shown in the plan view of the proximal end of FIG. 6. The first surface may be a slightly larger in diameter than the third surface. It may be seen in FIG. 7 that there will be a comparatively thin cross-section where the roots of the external thread 212 coincide with the internal thread. It may be advantageous to arrange the internal threads so that the roots coincide with the crest of the external thread to avoid a thin cross section.

The anchoring element 200 may be relatively short such that if the first and/or third generally cylindrical surfaces include a conical section, the conical section may occupy all or substantially all of the first and/or third surfaces.

FIGS. 9 through 13 illustrate another anchoring element 300 that embodies the invention. This embodiment includes many features that are similar to the anchoring element 100 illustrated by FIGS. 1 through 4. Similar features for anchoring element 300 have been given reference numerals that are the reference numerals used for anchoring element 100 increased by 200.

Figure 10:
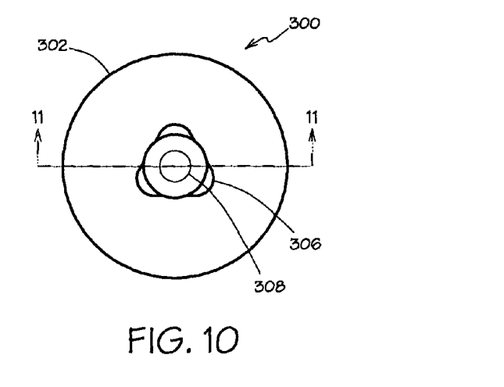
FIG. 10 is a plan view of the proximal end of the anchoring element of FIG. 9.
Figure 11:
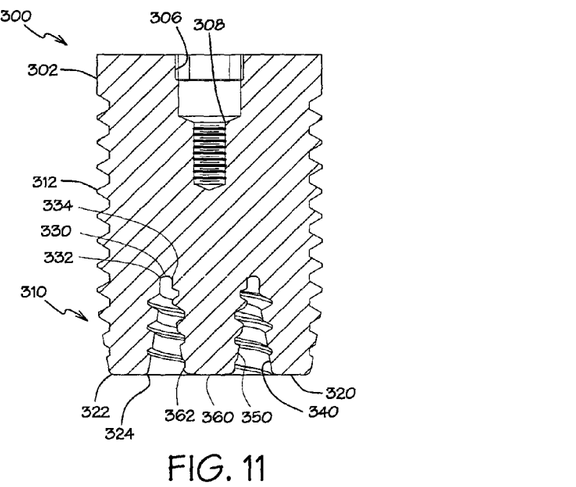
FIG. 11 is a cross section of the anchoring element taken along the line 11-11 shown in FIG. 10.

FIGS. 10 and 11 illustrate an abutment surface that may be provided to receive a dental prosthesis. The illustrated abutment surface includes a lobed locating recess 306 and an internal anchoring thread 308 to receive a devices that is coupled to the anchoring element 300 by a screw. The lobes of the locating recess 306 may prevent rotation of a coupled device and may provide a wrenching surface for embedding the anchoring element 300.

In this embodiment the anchoring element the fourth surface 330 is annular. The anchoring element further includes a fifth surface 350 concentric with the first surface and joined to the fourth surface 330 along an inner circumference 334 of the fourth surface. A sixth surface 360 is disposed toward the distal end of the first surface and joined to the fifth surface 350 along an outer circumference 362 of the sixth surface.

The fifth surface 350 may include a second external thread on all or part of the fifth surface. The second external thread has the pitch of the first external thread such that all threads will advance the anchoring element 300 at the same rate as it is rotated to embed the anchoring element into bone. The second external thread may be of any of a variety of forms known or discovered to be effective for embedding the anchoring element in bone. The second external thread may include self-threading (thread cutting) features or other features that aid in embedding the anchoring element into bone or that promote osseointegration. It is contemplated that the hole in the bone that is prepared to receive the anchoring element 300 may provide a secondary hole in the residual bone such that the fifth surface 350 will at least partially engage the bone to provide additional initial stability and an additional surface for osseointegration.

The fifth surface 350 may include a frustrated third conical portion adjacent the distal end such that a smaller circumference of the third conical portion is adjacent the distal end. The third conical portion may be unthreaded or may partially or fully intersect the second external thread on the fifth surface 350. In one embodiment the third conical portion may have a smallest diameter at the distal end of the anchoring element 300 that is approximately a root diameter of the second external thread. The third conical portion may gradually increase in diameter toward the proximal end thereby providing a gradually increasing thread depth. The second and third conical sections may act to compress the residual bone between the third and fifth generally cylindrical surfaces.

Figure 12:
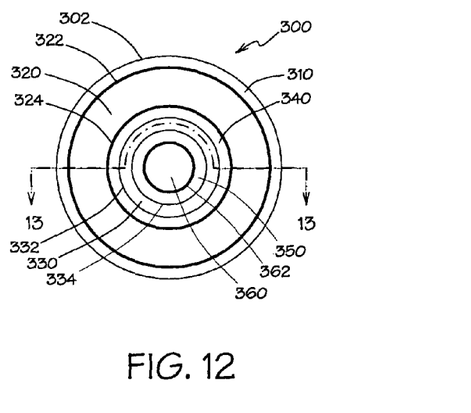
FIG. 12 is a plan view of the distal end of the anchoring element of FIGS. 9 through 11.
Figure 13:
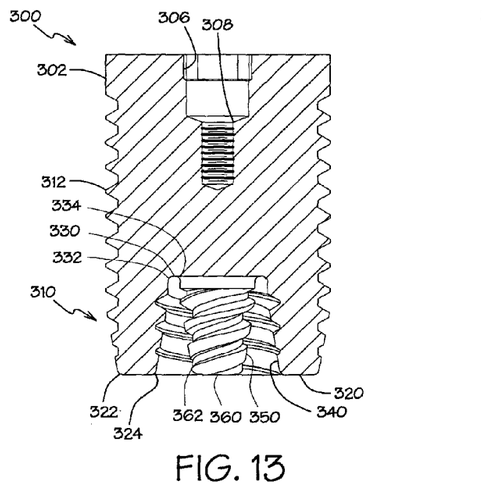
FIG. 13 is a cross section of the anchoring element with the distal portion taken along the section line 13-13 shown in FIG. 12 and the proximal portion taken along the section line 11-11 shown in FIG. 10.

FIG. 13 is a cross-section view of anchoring element 300 shown in FIGS. 9-12 where the lower part of the cross-section is taken along section line 13-13 shown in FIG. 12 so that the fifth surface is not cut by the cross-section and the fifth surface may be seen. The portion of the cross-section between the fourth surface 330 and the proximal end is taken along section line 11-11 shown in FIG. 10.

Figure 14:
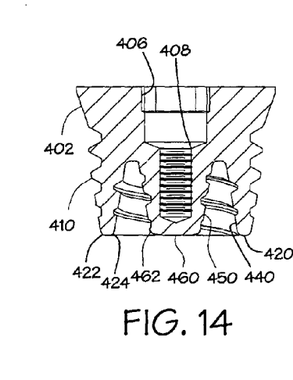
FIG. 14 is a cross section view of another anchoring element that embodies the invention.
Figure 15:
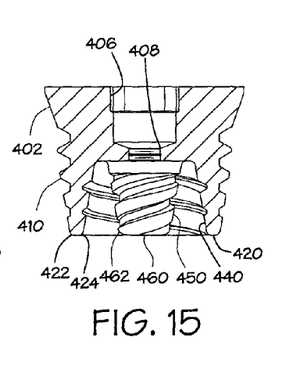
FIG. 15 is a cross section of the anchoring element shown in FIG. 14 with the distal portion sectioned similarly to the view of FIG. 13.

FIGS. 14 and 15 illustrate another anchoring element 400 that embodies the invention. This embodiment includes many features that are similar to the anchoring element 300 illustrated by FIGS. 9 through 13. Similar features for anchoring element 400 have been given reference numerals that are the reference numerals used for anchoring element 300 increased by 100.

In this embodiment the anchoring element 400 the first surface includes a shoulder surface 402 in the form of a frustrated conical section. Such a conical shoulder is intended to be included by the term "generally cylindrical." The anchoring element 400 may be relatively short such that an internal anchoring thread 408 extends into the portion of the anchoring element 400 defined by the fifth surface 450.

FIGS. 16 through 20 illustrate an exemplary use of an anchoring element 500 that embodies the invention to provide a dental prosthesis for an extracted molar tooth.

Figure 16:
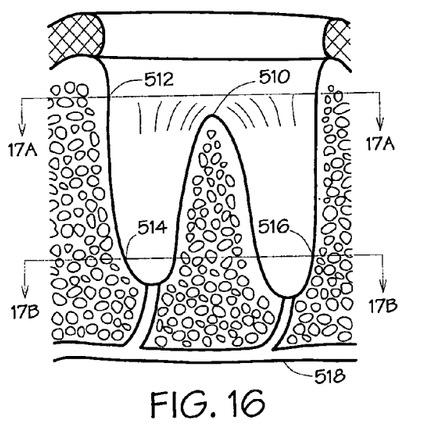
FIG. 16 is a cross section of a mandibular molar extraction site.

FIG. 16 shows a cross-section of a socket following the extraction of a mandibular molar having two roots. The cross-section is taken along a section line that is mesiodistal (running from the front to the back of the head). The socket includes the interradicular bone 510 which separated the roots of the extracted molar.

Figure 17:
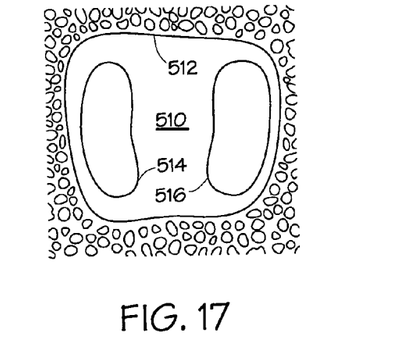
FIG. 17 is a cross section of the extraction site shown in FIG. 16.

FIG. 17 shows a cross-section of the socket viewed from the top and looking down into the socket. An outline of the cervical collar 512 taken along section line 17A-17A in FIG. 16 is shown. An outline of each of the two roots 514, 516 taken along section line 17B-17B in FIG. 16 is shown.

Figure 18:
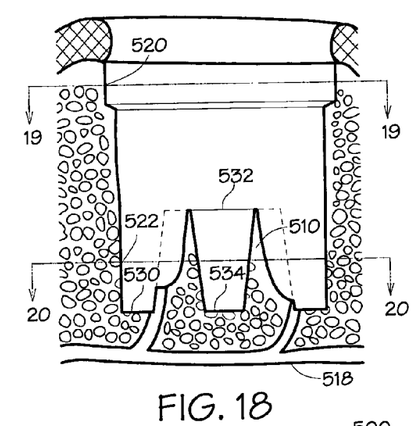
FIG. 18 is a cross section similar to the view of FIG. 16 showing the preparation of the extraction site for embedding an anchoring element.
Figure 19:
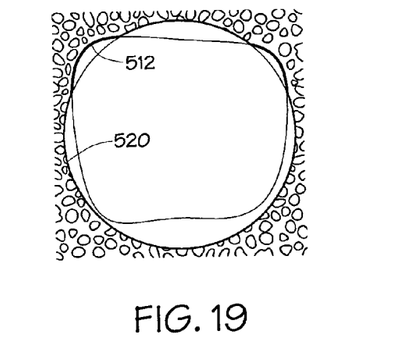
FIG. 19 is a cross section of the upper portion of the extraction site shown in FIG. 18.

FIG. 18 shows a cross-section of a prepared molar socket which is the socket of FIG. 16 after a hole has been prepared to receive the anchoring element. FIG. 19 is a top down cross-section of the prepared molar socket at the cervical collar 512 taken along section line. 19-19 in FIG. 18. It may be seen the prepared hole 520 may not remove all of the cervical collar 512. Generally it is desirable to provide a large periphery of contact between the anchoring element 500 and the cervical collar 512 to provide good initial stability. However, it is also desirable to preserve as much bone as possible consistent with preparing a hole that will provide good initial stability and good osseointegration. In particular, the bone may have a relatively thin and hard cortical layer surrounding a softer inner core of cancellous bone. It is desirable preserve the cortical bone which will provide much more initial stability than the spongy cancellous bone.

The anchoring element 500 may be sized to come within at least 1.5 millimeters of all parts of the socket so that osseointegration will occur. The anchoring element 500 may be sized so that about 75% or more of the periphery at the cervical collar is in direct contact with the anchoring element to provide good initial stability.

Figure 20:
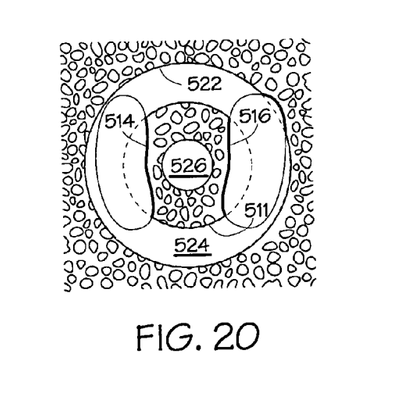
FIG. 20 is a cross section of the lower portion of the extraction site shown in FIG. 18.
Figure 21:
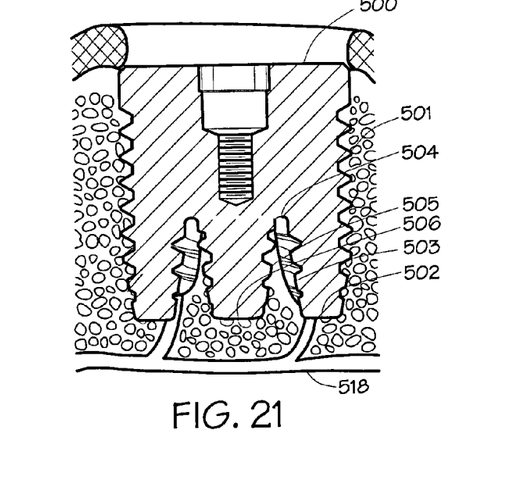
FIG. 21 is a cross section of an anchoring element embedded in the extraction site prepared as shown in FIG. 18.
Figure 22:
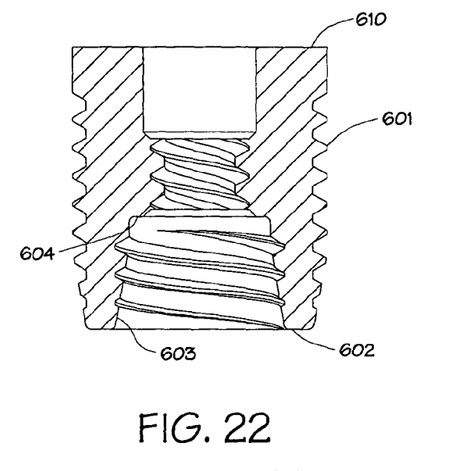
FIG. 22 is a cross section of a first part of another anchoring element that embodies the invention.
Figure 23:
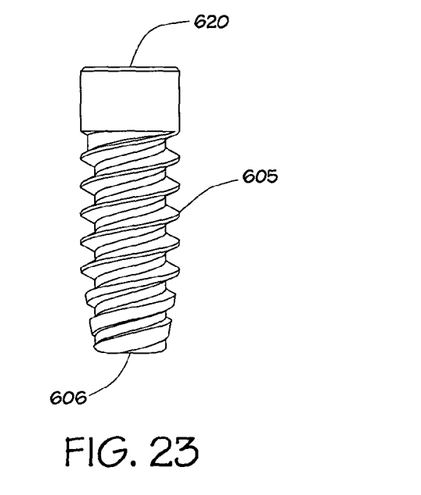
FIG. 23 is a side view of a second part of the anchoring element.

FIG. 20 shows a cross-section of the socket of FIG. 16 after a hole has been prepared to receive the anchoring element. FIG. 20 is a top down cross-section of the prepared hole at the roots 514, 516 taken along section line 20-20 in FIG. 18. It may be seen the prepared hole 522 may not remove all of the socket that surrounded the roots. It may also be seen that a substantial portion of the interradicular bone 510 is preserved as residual bone in the prepared molar socket. The distal portion of the prepared hole 522 includes an annular region 524 to receive the portion of the anchoring implant between the first surface 501 and third surface 503. The second surface 502 of the anchoring element 500 may bear against the bottom surface 524 of the molar socket 522 to increase initial stability of the anchoring element.

The bottom surfaces 530, 532, 534 of the prepared hole are also significant. It is desirable that the bottom surfaces support a significant portion of one or more of the second surface 502, fourth surface 504, and sixth surface 506 (if present) of the anchoring element 500. For this reason, the hole may be prepared with bottom surfaces 530, 534 that are below the lowest point of the roots if permitted by other anatomical structures such as the mandibular nerve 518 or maxillary sinus. A flat surface 532 may be prepared on the proximal portion of the residual interradicular bone 510 to support the fourth surface 504. The flat surface 532 on the proximal portion of the residual interradicular bone 510 may be generally parallel to the bottom surface 530 of the prepared molar socket 500.

The first surface 501 of the anchoring element 500 is adapted to threadedly engage the outer wall 522 of the molar socket. The first surface 501 may include a frustrated first conical portion adjacent the second surface 502 such that a smaller circumference of the first conical portion is adjacent the second surface. The conical surface may aid in placing the anchoring element into the prepared molar socket. The conical surface may compress the bone surrounding the outer wall of the prepared molar socket, particularly in the upper portion adjacent the cervical collar, which may increase bone density and support for the anchoring element.

The third surface 503 of the anchoring element 500 is adapted to bear against a first surface 511 of the interradicular bone 510 that generally faces the outer wall 522 of the molar socket. The third surface 503 may have a frustrated conical form such that it may compress the interradicular bone, particularly in the upper portion, which may increase bone density and support for the anchoring element 500. The third surface 503 may include screw threads, which may be self-cutting threads, for threadedly engaging the first surface 511 of the interradicular bone 510.

The anchoring element 500 may include a fifth surface 505. The prepared molar socket may therefore include a secondary hole 526 in the residual interradicular bone 510 to receive the fifth surface 505. The fifth surface may bear against a side wall of the secondary hole. The fifth surface 505 may have a frustrated conical form such that it may compress the interradicular bone, particularly in the upper portion, which may increase bone density and support for the anchoring element 500. The fifth surface 505 may include screw threads, which may be self-cutting threads, for threadedly engaging the side wall of the secondary hole 526.

Figure 24:
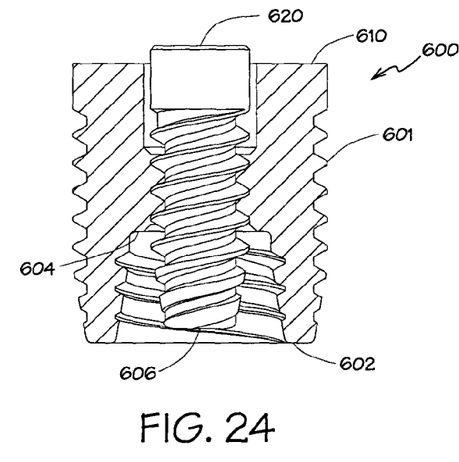
FIG. 24 is a view of the second part shown in side view installed into the first part shown in cross section to form the anchoring element.
Figure 25:
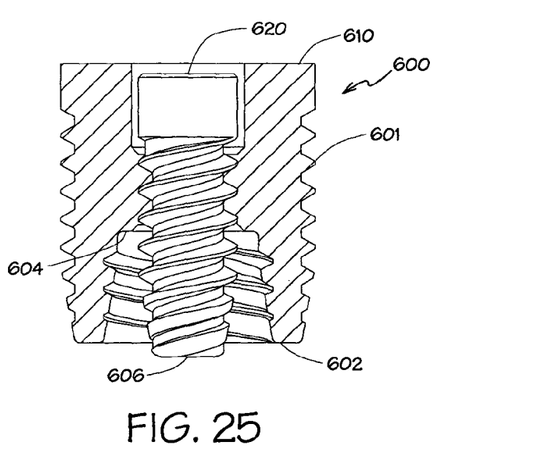
FIG. 25 is a view of an alternate position for the second part relative to the first part of the anchoring element shown in FIG. 24.

FIGS. 22 through 25 show another anchoring element 600 that embodies the invention. A first part 610 includes a first surface 601, a second surface 602, a third surface 603, and a fourth surface 604. A second part 620 includes a fifth surface 605 and a sixth surface 606. The fifth surface 605 is joined to the fourth surface 604 by screwing the second part 620 into the first part 610. The resulting assembly provides an anchoring element 600 that has similar features to the anchoring element 300 shown in FIG. 9. It may be possible to adjust the position of the sixth surface 606 relative to the second surface 602 as shown by FIGS. 24 and 25.

Figure 26:
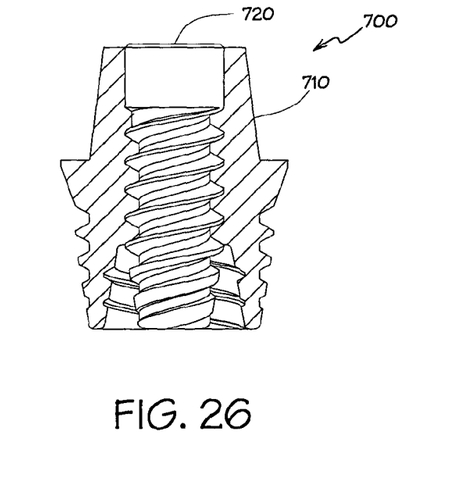
FIG. 26 is a cross section of a first part and side view of a second part forming another anchoring element that embodies the invention.

FIG. 26 shows another anchoring element 700 that embodies the invention. A second part 720 is screwed into a first part 710 to provide an anchoring element 700 that has similar features to the anchoring element 400 shown in FIG. 14. The second part 720 may be shaped so that it can screwed into an interference fit with the first part 710 such that the anchoring element 700 functions as a single piece after assembly.

Figure 27:
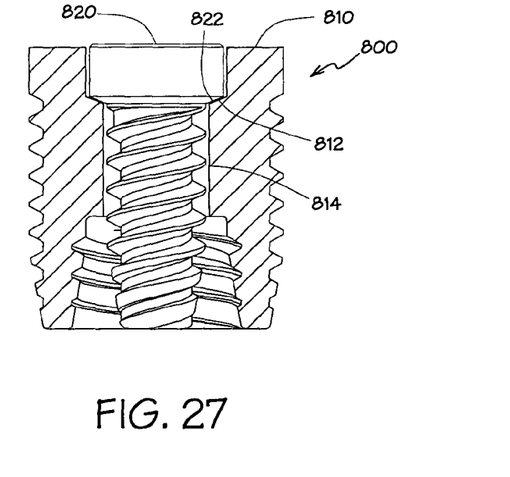
FIG. 27 is a cross section of a first part and side view of a second part forming another anchoring element that embodies the invention.

FIG. 27 shows another anchoring element 800 that embodies the invention. A second part 820 passes through an unthreaded opening 814 in a first part 810 to provide an anchoring element 800 that has similar features to the anchoring element 400 shown in FIG. 14. The second part 820 may include a head surface 822 that bears against a shoulder surface 812 on the first part when both parts are embedded in bone. When both parts are assembled into an anchoring element 800 by being embedded in bone, the second part 820 may be adjusted to change the distally directed pressure of the first part 810 against the bone.

Figure 28:
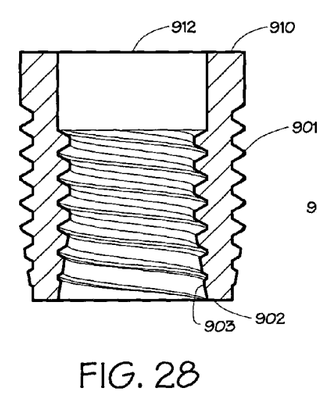
FIG. 28 is a cross section of a first part of another anchoring element that embodies the invention.
Figure 29:
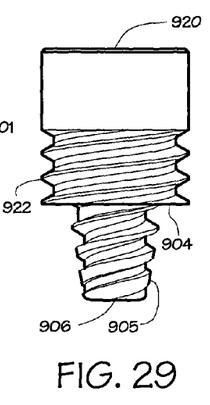
FIG. 29 is a side view of a second part of the anchoring element.
Figure 30:
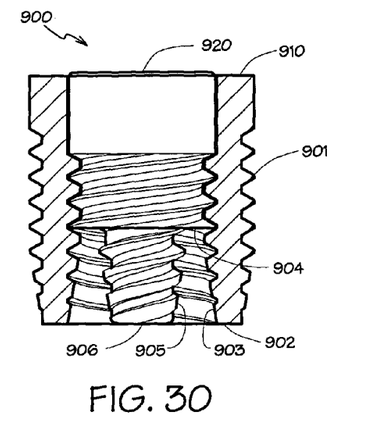
FIG. 30 is a view of the second part shown in side view installed into the first part shown in cross section to make the complete anchoring element.

FIGS. 28 through 30 show another anchoring element 900 that embodies the invention. A first part 910 includes a first surface 901, a second surface 902, and a third surface 903. The third surface 903 extends from the distal end to the proximal end providing a through passage that includes an internal thread for a least a portion of the third surface. A second part 920 includes a fourth surface 904, a fifth surface 905, and a sixth surface 906. The second part 920 further includes a joining surface 922 that is generally cylindrical and concentric with the fifth surface 905. At least a portion of the joining surface may include an external thread that mates with at least a potion of the threaded third surface 903 of the first part 910. The third surface 903 is joined to the fourth surface 904 by screwing the second part 920 into the first part 910. The resulting assembly provides an anchoring element 900 that has similar features to the anchoring element 300 shown in FIG. 9.

Figure 31:
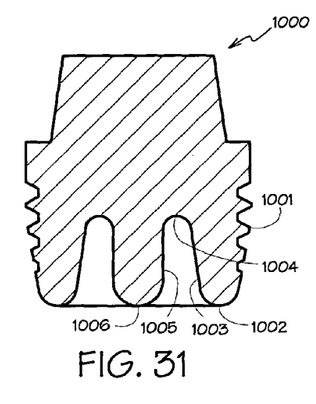
FIG. 31 is a cross section of another anchoring element that embodies the invention.

FIG. 31 shows another anchoring element 1000 that embodies the invention. This embodiment includes a first surface 1001, a second surface 1002, a third surface 1003, a fourth surface 1004, a fifth surface 1005, and a sixth surface 1006 similarly arranged to previously described embodiments. In this embodiment the second surface 1002, fourth surface 1004, and sixth surface 1006 may be curved. In this embodiment, only the first surface 1001 may include a threaded portion. The fifth surface 1005 may be a right cylinder such that this portion of the anchoring element 1000 may fit into a pilot hole that may have been used to guide the preparation of the bone to receive the anchoring element. The second surface 1002 may include a conical portion to provide a close fit to residual bone.

Figure 32:
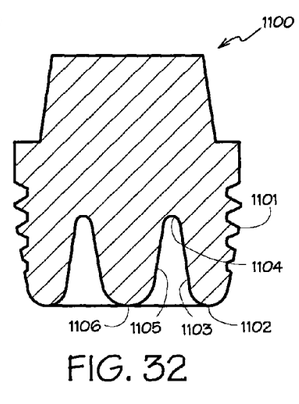
FIG. 32 is a cross section of another anchoring element that embodies the invention.

FIG. 32 shows another anchoring element 1100 that embodies the invention. This embodiment includes a first surface 1101, a second surface 1102, a third surface 1103, a fourth surface 1104, a fifth surface 1105, and a sixth surface 1106 similarly arranged to previously described embodiments. The anchoring element 1100 of this embodiment is generally similar to the anchoring element 1000 of FIG. 31. The fifth surface 1105 and the second surface 1102 may include conical portions to provide a close fit to residual bone.

Figure 33:
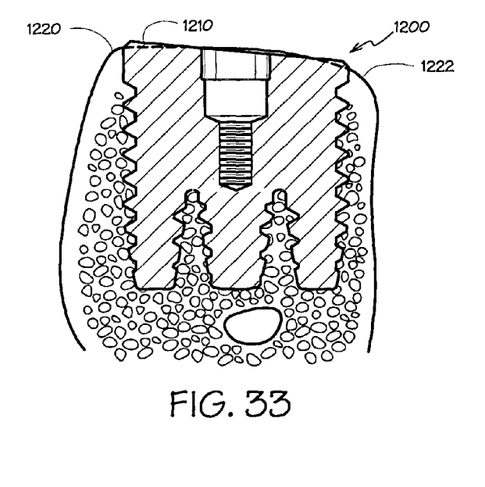
FIG. 33 is a cross section of another anchoring element that embodies the invention shown as it may be embedded in bone.

FIG. 33 shows another anchoring element 1200 that embodies the invention. FIG. 33 is a cross-section of the anchoring element 1200 embedded in the posterior portion of a mandible along section line in a bucco-lingual (cheek to tongue) direction. This embodiment includes an abutment surface 1210 that is at an angle to an axis from the proximal end to the distal end of the first surface. The abutment surface 1210 may be substantially flat in the area adjacent the proximal end of the first surface 1201. As shown in FIG. 33, when an anchoring element is embedded in a healed molar extraction site, resorption of the bone may cause the site to be shallow with a surface that may be higher on one side 1220 than the other 1222, generally being lower to the buccal (cheek) side 1222. It may be seen that the angled abutment surface 1210 allows the first surface 1201 to have greater contact with the bone without leaving a portion of the anchoring element 1201 exposed above the bone.

Figure 34:
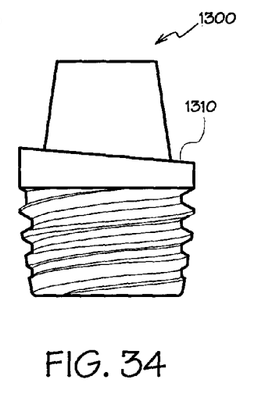
FIG. 34 is a side view of another anchoring element that embodies the invention.

FIG. 34 shows another anchoring element 1300 that includes an abutment surface 1310 that is at an angle to an axis from the proximal end to the distal end of the first surface.

Figure 35:
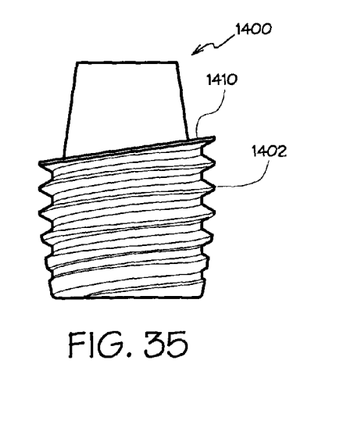
FIG. 35 is a side view of another anchoring element that embodies the invention.

FIG. 35 shows another anchoring element 1400 that includes an abutment surface 1410 that is at an angle to an axis from the proximal end to the distal end of the first surface. In this embodiment the threaded portion of the first surface may extend to the abutment surface which may increase the threaded engagement of the anchoring element 1400 to bone.

Figure 36:
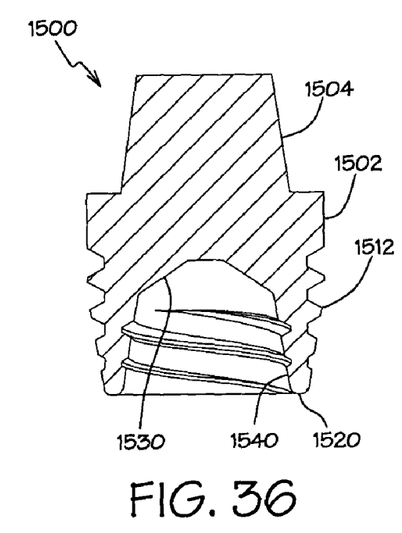
FIG. 36 is a cross section of another anchoring element that embodies the invention.

FIG. 36 shows another anchoring element 1500 that embodies the invention. This embodiment includes many features that are similar to the anchoring element 200 illustrated by FIGS. 5 through 8. Similar features for anchoring element 1500 have been given reference numerals that are the reference numerals used for anchoring element 200 increased by 1300. The anchoring element 1500 includes a fourth surface 1530 disposed between the distal end and the proximal end and joined to the third surface 1540. The fourth surface 1530 is in the form of a frustrated cone. It is contemplated that the hole in the bone that is prepared to receive the anchoring element 1500 may leave an upper surface on the residual interradicular bone such that the fourth surface 1530 will engage the upper surface to provide additional initial stability and an additional surface for osseointegration. The conical shape of the fourth surface may allow the residual interradicular bone to be selectively compressed as determined by how far into the molar socket the anchoring element 1500 is advanced. This may allow a greater degree of compression to be applied when the residual interradicular bone is soft and spongy.

Figure 37:
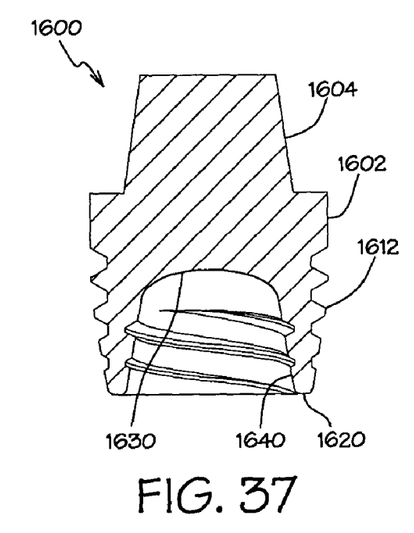
FIG. 37 is a cross section of another anchoring element that embodies the invention.

FIG. 37 shows another anchoring element 1600 that embodies the invention. This embodiment includes many features that are similar to the anchoring element 200 illustrated by FIGS. 5 through 8. Similar features for anchoring element 1600 have been given reference numerals that are the reference numerals used for anchoring element 200 increased by 1400. The anchoring element 1600 includes a fourth surface 1630 disposed between the distal end and the proximal end and joined to the third surface 1640. The fourth surface 1630 is in the form of a convex curved surface. It is contemplated that the hole in the bone that is prepared to receive the anchoring element 1600 may leave an upper surface on the residual interradicular bone such that the fourth surface 1630 will engage the upper surface to provide additional initial stability and an additional surface for osseointegration. The convex shape of the fourth surface may allow the residual interradicular bone to be selectively compressed as determined by how far into the molar socket the anchoring element 1600 is advanced. This may allow a greater degree of compression to be applied when the residual interradicular bone is soft and spongy.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. It is to be understood that individual features shown or described for one embodiment may be combined with individual features shown or described for another embodiment. It is to be understood some features are shown or described to illustrate the use of the invention in the context of functional anchoring elements and such features may be omitted within the scope of the invention.

What is claimed is:

1. A dental implant for supporting a dental restoration in a jawbone, the dental implant comprising:
    a body extending along a longitudinal axis and having a coronal end and an apical end, the coronal end forming, in part, an abutment surface that extend generally transverse to the longitudinal axis of the dental implant and the apical end, in part, forming an annular surface that extends generally transverse to the longitudinal axis of the dental implant;
    an external surface extending between the abutment surface and the annular surface and generally facing away from the longitudinal axis of the dental implant at least a portion of the external surface including an external thread having a pitch;
    a first inner surface concentric with the external surface, the inner surface generally facing towards the longitudinal axis of the dental implant and joined to the annular surface along an inner circumference of the annular surface on the apical end of the dental implant, at least a portion of the inner surface including an internal thread having the pitch of the external thread;
    a second annular inner surface that is joined to the first inner surface along an outer circumference of the second inner surface and extends generally transverse to the longitudinal axis of the dental implant and faces in a generally apical direction;
    a third inner surface concentric with the external surface and joined to the second annular inner surface along an inner circumference of the second annular inner surface, the third inner surface generally facing away from the longitudinal axis of the dental implant, at least a portion of the third inner surface including a second external thread having the pitch of the external thread; and
    an apical surface that faces in a generally apical direction and is joined to the third inner surface along an outer circumference of the apical surface.

2. The dental implant of claim 1 wherein the first external surface includes a first conical portion adjacent the apical end such that a smaller circumference of the first conical portion is adjacent the apical end.

3. The dental implant of claim 1 wherein the first inner surface includes a conical portion adjacent the apical end such that a larger circumference of the conical portion is adjacent the apical end.

4. The dental implant of claim 1 wherein the internal thread and the first external thread are such that both threads will advance the anchoring element at the same rate as the anchoring element is rotated to embed the anchoring element into bone.

5. The dental implant of claim 1 wherein the internal thread is self-threading.

6. The dental implant of claim 1, wherein the third inner surface includes a conical portion adjacent the apical surface a smaller circumference of the conical portion is adjacent the apical end.

7. The dental implant of claim 1,
    wherein the external surface, the abutment surface, the annular surface, the first inner surface and the second inner surface form a first part of the dental implant; and
    the third inner surface and the apical surface form a second part; and
    the third inner surface is placed adjacent to the second inner surface by passing the second part through the first part.

8. The dental implant of claim 1,
    wherein the external surface, the abutment surface, the annular surface and the first inner surface form a first part of the dental implant;
    the second inner surface, the third inner surface and the apical surface form a second part of the dental implant; and
    the second inner surface is placed adjacent to the first inner surface by passing the second part through the first part.

9. The dental implant of claim 1 wherein the abutment surface defines in part a conical surface that is at an angle to the longitudinal axis of the dental implant.

10. The dental implant of claim 1, wherein the abutment surface includes an external hex surface.

11. The dental implant of claim 1, wherein the abutment surface includes an frustrated square pyramid for supporting a dental prosthesis.

12. The dental implant of claim 1, wherein the abutment surface is configured to be directly coupled to a prosthetic tooth.

13. The dental implant of claim 1, the abutment surface includes a lobed recess and an internal anchoring thread to receive an abutment coupled to the abutment surface by a screw.

14. The dental implant of claim 1, wherein the abutment surface is substantially perpendicular to the longitudinal axis of the dental implant.

15. The dental implant of claim 1, wherein the annular surface is substantially perpendicular to the longitudinal axis of the dental implant.

16. The dental implant of claim 1, wherein the external surface defines includes an unthreaded shoulder adjacent the abutment surface.

* * * * *